United States Patent [19]

Lebrun et al.

[11] 4,442,091

[45] Apr. 10, 1984

[54] PROCESS FOR COMBATTING AND/OR PREVENTING ALLERGIC DISEASES EMPLOYING NATAMYCIN

[75] Inventors: Philippe Lebrun, La-Neuve; Daniele de Saint Georges-Gridelet, Geel, both of Belgium

[73] Assignee: Gist-Brocades N.V., Delft, Netherlands

[21] Appl. No.: 377,205

[22] PCT Filed: Aug. 28, 1981

[86] PCT No.: PCT/NL81/00024

§ 371 Date: Apr. 29, 1982

§ 102(e) Date: Apr. 29, 1982

[87] PCT Pub. No.: WO82/00750

PCT Pub. Date: Mar. 18, 1982

[30] Foreign Application Priority Data

Aug. 29, 1980 [NL] Netherlands .......................... 8004949

[51] Int. Cl.[3] .............................................. A01N 63/02

[52] U.S. Cl. ...................................................... 424/181
[58] Field of Search ........................................... 424/181

[56] References Cited

U.S. PATENT DOCUMENTS 3,892,850  7/1975  Struyk et al. ........................ 424/119

OTHER PUBLICATIONS

Bronswijk et al.; vol. 77, 15, 518p (1972).
Leysen et al., vol. 83, 54, 531f (1975).
"Rote Liste" (1979) #20020B and #20021B Primary Examiner—Allen J. Robinson
Attorney, Agent, or Firm—Bierman, Bierman & Peroff

[57] ABSTRACT

The invention provides a method for combatting and-/or preventing allergic diseases which are caused by house-dust mites by treating said mites or places or areas which are afflicted or may be afflicted by said mites with an effective amount of natamycin.

6 Claims, No Drawings

PROCESS FOR COMBATTING AND/OR PREVENTING ALLERGIC DISEASES EMPLOYING NATAMYCIN

The invention relates to a process for combatting and/or preventing allergic diseases and more particularly those allergic diseases which are caused by house-dust mites.

For a long time allergic diseases were supposed to be caused by tiny vegetable pollens in the atmosphere. Later on it was supposed that these diseases could also be caused by the abundance of mould spores.

Although intensive research was carried out for many years, efficient means for combatting allergic diseases, particularly those actually caused by house-dust mites and more particularly those occurring in mattress-dust and the like did not become available up to now.

From Mykosen 20(3), 101–106 it is known that fungi belonging to the species of *Aspergillus glaucus* and *Aspergillus restrictus* play a role in the ecology of the house-dust mites and in the origination of the house dust allergen, while Mykosen 18(9), 385–392 discloses the results of a study of a presumed interaction between *Tyrophagus putrescentiae* and some fungi.

A presumed interaction of several fungi with *Dermatophagoides farinae, Dermatophagoides pteronyssinus* and *Euroglyphus maynei* was also described, see for example Environ. Entomol. 2(1), 142–145 (1973), Oecologia (Berl) 33(3), 351–360 (1978) and Oecologia (Berl) 36(1), 81–92, (1978).

Furthermore, it is known to destroy other types of mites which are found in agricultural products or to inhibit their development by applying mixtures of fungicides and/or pesticides with a variety of molecular structures, see for example Japanese patent applications 79/101.426 and 77/076.428.

Several methods have been tried in order to influence the presumed relationship between the growth of fungi in dry domestic dust on the one hand and the occurrence and growth of house-dust mites on the other hand. For example, in J. Med. Entomol. 8, 748 (1971) the use of the fungicide Nipagin ® (methyl p-hydroxybenzoate) is described in the control of house-dust mites and microorganisms, but only under laboratory conditions. However, these proposed methods did not give rise to an adequate combatting method for the aforementioned allergic diseases up to now, because the agents used were not sufficiently active or showed an unacceptable high toxicity and/or caused allergic reactions.

Surprisingly, as a result of extensive research and experimentation a process was now found for an adequate combatting method of allergic diseases, which are mainly caused by house-dust mites and more particularly by species of *Dermathophagoides pteronyssinus* and *Dermathophagoides farinae*.

It has been found that these species live in combination and interaction with certain specific fungi, which are naturally present in house-dust and more particularly in mattress-dust. The most important fungi in this connection were found to be *Aspergillus penicilloides, Aspergillus glaucus* and *Aspergillus restrictus*. Of these, *Aspergillus penicilloides* appeared the most important factor for the growth, survival and reproduction of house-dust mites.

It has now been found that the use of a particular fungicide, natamycin, caused an effective inhibitory effect on the growth, development and reproduction of house-dust mites, which resulted in an important decrease of certain allergic affections.

Thus, the present invention relates to a process for combatting and/or preventing allergic diseases which are caused by house-dust mites, characterised in that said mites or places or areas, which are afflicted or may be afflicted by said mites, are treated with an effective amount of natamycin.

The invention relates also to a composition for destroying house-dust mites and inhibiting the growth of populations of house-dust mites, particularly species of *Dermatophagoides pteronyssinus* and *Dermatophagoides farinae*, which comprises an effective amount of natamycin in conjunction with a vehiculum or carrier.

The invention relates further to mattresses, bedding and the like, which are treated with of natamycin for destroying house-dust mites and inhibiting growth of populations of such mites.

Usually, the natamycin is applied in suspended form in water for the purpose of this invention. A suitable concentration range for such suspension is from about 0.1 to about 30% w/v, preferably from about 1 to about 15% w/v and most preferably from about 2 to about 5% w/v. In certain cases it may be useful to add preserving and wetting agents to the suspension. An example of such agent is benzalkonium chloride. Another useful preserving treatment of the suspension is the treatment with $N_2O$.

Also suitable are suspensions of natamycin in a rapidly and completely or practically completely evaporating non-toxic, inert organic solvent or a mixture of solvents.

Other compositions of natamycin, for example natamycin admixed with an inert carrier may also be used for the purpose of this invention.

Preferably, a finely divided powder or a suspension of natamycin, formerly known as pimaricin, is sprayed for that purpose on house-dust containing or bearing surfaces, for example room walls, room floors, furniture etc. and more particularly mattresses, blankets, bed clothes, eiderdown quilts, and the like.

Effective amounts of natamycin to be used according to the invention were found to be in the range of 0.5–20% by weight based on the weight of the substrate treated in laboratory in vitro experiments. More particularly, the effective amount is about 5–10% by weight when the treatment is carried out one to eight times and preferably three to six times with time intervals of one to four weeks and preferably of about two weeks.

The number of treatments and the amount of natamycin to be used are dependent on a number of factors, such as the season, mite phenology, relative humidity of atmosphere, temperature, condition of the sufferer and change of acaricide activity previously studied in the laboratory. For example, when treating a mattress wherein the house-dust mites and fungi were supposed to stay, a dose of natamycin of about 0.1 to about 1.0 $g/m^2$, preferably about 0.25 $g/m^2$, the number and frequency of treatments being as mentioned before, led to successful results.

According to a preferred embodiment of the invention an effective aqueous natamycin suspension to be sprayed according to the purpose of the invention is obtained from micronized natamycin powder and water, to which, preferably, a wetting agent such as benzalkonium chloride is added. Preferably, the suspension is sprayed with the aid of a suitable propellant, such as butane, propane, carbon dioxide, a chlorofluorohydrocarbon, etc.

The compositions of the aqueous natamycin suspensions according to the invention are preferably in unit-dose form. A preferred unit-dose form contains for example 0.5 g of natamycin, 0.004 g of benzalkonium chloride, 15 ml of destilled water and 4 g of butane.

An important advantage of natamycin is that it does not show any toxic or allergic reactions at all when used in a composition according to this invention.

It is true that it is known from U.S. Pat. No. 3,892,850 column 3, table III that *Aspergillus niger* and *Aspergillus fumigatus* species may be inhibited by pimarcin (natamycin), but no indication whatsoever is given relating to inhibition of the growth of Aspergillus species, which are presently mainly involved and especially not with respect to *Aspergillus penicilloids*. Besides, it is known from the thesis of B. v.d. Lustgraaf, "Ecological relationships between microorganisms and house-dust mites (Acarida: Pyroglyphidae)", September 1978, page 9, that *Aspergillus niger* and *Aspergillus tawamari* species have an unfavourable influence on mites.

From German patent application 25 29 532 (pages 3, 4, 20 and 21), it is known that in order to reach effective inhibition of the growth of fungi and spores, special natamycin containing compositions had to be prepared with the aid of specially selected auxiliaries.

Therefore, it will be appreciated that persons skilled in the art would certainly not be inclined to select primarily the antibiotic natamycin for combatting allergic diseases and would rather select another compound from the large amount of known fungicides, in order to avoid the aforementioned problems. Moreover, the natamycin containing compositions which are disclosed in said German patent application 25 29 532, cannot be applied in any way as such for spraying on mattresses, bed clothes and the like.

It will be appreciated that the attractive results which are obtained with the process could definitely not be predicted or expected by people skilled in the art. Certainly not, when having in mind the initially negative results of the treatment in laboratory experiments with natamycin of in vitro pure cultures of isolated house-dust mites and the rather long period of time between the published assumption of an interaction of mites and fungi and the present invention. Moreover, natamycin has not shown any hypersensitivity up to now, on contrast with other known fungicides such as Nipagin ®, cf. A Araujo-Fontaine, "Acarariens et allergie à la poussière. Essais de détermination des IgE spécifiques vis-a-vis des Acariens (*D.pteronyssinus* et *D.farinae*) par la methode des immunoabsorbants", Thesis University of Louis Pasteur, Strasbourg, 1974.

The surprising element of the choice of natamycin from the large group of known fungicides also appears from the fact that in comparative experiments with natamycin and the widely used fungicide nystatin on the development of populations of *Dermatophagoides pteronyssinus* and *Dermatophagoides farinae* the total populations were decreased considerably more after treatment with natamycine than after a similar treatment with nystatin.

Moreover, the activity of nystatin on gravids of said Dermatophagoides species appeared to be much less significant as compared to natamycin, i.e. the percentage of surviving gravids after treatment with nystatin is larger than after treatment with natamycin.

The invention is illustrated by the following Examples. However, it should be understood that the invention is not intended to be limited to the specific embodiments.

EXAMPLE 1 a. Experimental

In vitro experiments were carried out, consisting of sequential treatments following the next scheme:
5 series of 12 replications (microcosms) each and each with 10 males and 10 females of *D.pteronyssinus* (newly emerged)
3 incubation times, namely 2, 4 and 6 weeks
1. one series (Exp 1) inoculated with *Aspergillus penicilloides* and once treated with natamycin (10%), namely 4 weeks after incubation
2. one series (Exp 2) inoculated with *Aspergillus penicilloides* and twice treated with natamycin (10%), namely 2 weeks and 4 weeks after incubation
3. one series (Exp 3) inoculated with *Aspergillus penicilloides* and three times treated with natamycin (10%), namely just after the start of the incubation and 2 weeks and 4 weeks after incubation.
4. one series (Contr 1) inoculated with *Aspergillus penicilloides* in excess and not treated
5. one series (Contr 2) not inoculated and not treated.
However, *Aspergillus penicilloides* is naturally present in the digestive tract of the mites, because spores and mycelium were introduced in the tract and are not degraded (endozoochory).

In each of the 5 series 4 replications were entirely counted (males, females (gravids or not), number of eggs, larves and nymphs) after 2, 4 and 6 weeks.

b. Preparation of culture media

The experiments were conducted on standardized mattress-dust, namely which was collected at different places from different types of bedding. This was performed in order to obtain a mean culture medium which may be considered as representive as possible for cosmopolitan house-dust.

After having homogenised this medium the dust was divided into 60 microcosms of 25 mg each and sterilised for 72 hours with U.V. The efficacy of sterilisation was checked and found 100%.

c. Isolation of fungi

A culture medium was prepared in a Petri dish from malt agar and 64% of sucrose. Bodies of female acari were then put on this medium and cut open. The acari were first sterilised by immersion in a 1% solution of sodium hypochlorite for 2 to 3 minutes, rinsed with sterile water and dried on sterile filter paper.

After an incubation period of 21 days at 25° C., spores of *Aspergillus penicilloides* were isolated.

This method of cultivating *Aspergillus penicilloides* was preferred rather than using a strain coming from a fungi bank, because such strains could differ from the wild ones.

d. Action of fungi

Since *Aspergillus penicilloides* is presumed to stimulate the growth of home-dust mites, it is important to have it on the culture medium before the colonisation of the substrates by the *Dermatophagoides pteronyssinus*.

Therefore, a great number of spores of *Aspergillus penicilloides* were brought on the media 3 days before the introduction of the mites. The isolated spores were suspended in 1 ml of sterile water and one drop of this suspension was put on each of the 60 aliquots.

e. Action of natamycin

After 72 hours under optimal conditions for development of xerophilic fungi (temperature 25° C., relative humidity 75%), 2.5 mg of micronised natamycin were introduced as an aqueous suspension and mixed with each culture medium. Thus, the concentration of natamycin was 10% w/w in relation to the microcosms. Then 10 female and 10 male mites were put on each culture medium.

The mites used for these experiments were previously kept on a nutrient medium of a 1:1 mixture of human skin scales and dry yeast (*Saccharomyces cerivisiae*) under constant conditions. The temperature was kept at 25° C. and the relative humidity at 75%.

f. Results

The results of the experiments are represented in the drawing belonging to this specification.

It appeared that there is a marked influence on the growth in the different stades of development on treated medium. Protonymphs were still absent after two weeks of incubation. This phenomenon is the same for tritonymphs after 4 weeks of incubation.

It appeared also from the drawing that the percentage of reduction of living population after 6 weeks (number of living mites in the microcosms treated three times/number of living mites after 6 weeks in the controls) is 90% and 98% as compared with Contr. 1 and Contr. 2, respectively.

The survival time of adults of *Dermatophagoides pteronyssinus* was also strongly altered. For all stades the evolution of mortality was closely related to the sequential design of the treatments.

Furthermore, the fertility and thus the reproductive potential had diminished. The number of eggs and the number of gravide females were smaller in the replications treated with natamycin than in the non-treated ones.

EXAMPLE 2

A comparison was made of the effects of natamycin and the well-known fungicide nystatin on the growth of two species of house-dust mites, *Dermatophagoides pteronyssinus* and *Dermatophagoides farinae*.

Experimental conditions

Temperature 25° C.; relative humidity 75%.

Three treatments with 2.5 mg each of natamycin and nystatin, respectively, after 0, 2 and 4 weeks. The fungicide was introduced as an aqueous suspension (dropped with a pipette on the microcosms and mixed).

Microcosms of 25 mg of house-dust (concentration of natamycin: 10% w/w)+inoculation with *Aspergillus penicilloides*+10 couples of Dermatophagoides (newly emerged).

The results are summarized in the following Table A.

TABLE A

Comparison of effects of natamycin and nystatin on *Dermatophagoides pterpnyssinus* and *Dermatophagoides farinae*.

| | Treated with | | |
|---|---|---|---|
| | natamycin | nystatin | Controls |
| *D. pteronyssinus* | | | |
| X alive* | 18 | 47 | 503 |
| X dead* | 29 | 44 | 8 |
| % mortality | 62 | 47 | 2 |
| % gravid females | 0 | 12.5 | 59 |
| % reduction of population | 96 | 90 | — |
| *D. farinae* | | | |
| X alive* | 39 | 118 | 787 |
| X dead | 46 | 97 | 25 |
| % mortality | 54 | 45 | 3 |
| % gravid females | 0 | 20 | 61 |
| % reduction of population | 95 | 85 | — |

*Average of 4 replications (microcosms): balance after 6 weeks (number of eggs + larves + nymphs + adults).

It can be seen from the Table that the efficacy of natamycin on the reduction of populations of both *D. pteronyssinus* and *D. farinae* is very high (>95%) and significant better than of nystatin.

The superiority of natamycin over nystatin appears even more clearly from the blockage of reproduction (cf. the Table: the percentage of gravids is zero for both species, against 12.5 and 20% with nystatin).

EXAMPLE 3

A comparison was made of the effects of water, natamycin, Sephadex and talc, respectively, on the pulverization of the eggs of *Dermatophagoides pteronyssinus*. Said agents were sprayed on the eggs within 12 hours after laying. The spraying time was 5 seconds. The female mites were removed in order to exclude effects which could influence the experiment. For the same reason the hatched eggs were counted only after 30 days (the development of a normal egg under optimal conditions lasts 6 days).

The results (in triplicate) are summarized in the following Table B.

TABLE B

| | Number of treated eggs | Number of hatched eggs | % hatched (average) |
|---|---|---|---|
| Water | 89 | 89 | 99.1 |
| | 115 | 113 | |
| | 98 | 97 | |
| Natamycin (10%) | 107 | 0 | 0 |
| | 103 | 0 | |
| | 91 | 0 | |
| Sephadex (10%) | 94 | 91 | 96.6 |
| | 119 | 113 | |
| | 85 | 84 | |
| Talc (10%) | 83 | 54 | 70.2 |
| | 94 | 77 | |
| | 108 | 69 | |

It appeared that none of the eggs developed after treatment with natamycin.

EXAMPLE 4

A clinical experiment was performed with five patients who had an allergy to house-dust. Those patients developed a pathology of asthma.

The following technique was used. A suspension of 1 g of micronised natamycin in 10 ml of water was sprayed on the upper side of a mattress, on both sides of a pillow and, if present, on both sides of a bolster. Thus, the concentration obtained was about 0.5 g/m².

After drying in the air for about one hour the mattress and the pillow were covered with a sheet and a pillowcase, respectively.

The treatment was repeated every four weeks during 4 to 6 months (generally from the end of April to the beginning of November).

Each aspersion was preceded by collecting a dust sample from the mattress and the pillow by using a small vacuum cleaner for 4 to 5 minutes, as a result of which about 1 to 2 g of the mattress dust was obtained.

In each case comparative tests were performed by collecting dust samples from a mattress and a pillow of a bed placed in the same room, but not treated with natamycin. The samples were immersed in 96% alcohol in order to fix living populations (cf. Acarologia 17, 693–708 (1976)). A fraction of about 10 ml of suspended dust was each time integrally counted. Since the weights of the samples were different the counts were corrected and extrapolated to a standard dust sample of 500 mg.

It appears from the results that the control method was very effective in all periods investigated, in that the populations of house-dust mites from the bedding treated with natamycin were considerably decreased, whereas the non-treated populations multiplied.

At the same time, the condition of all patients who were in contact with and slept on the treated mattresses and bedding, improved significantly.

We claim:

1. A method of combatting house-dust mites comprising contacting house-dust mites with a miticidally effective amount of natamycin.

2. The method of claim 1 wherein the amount of natamycin is about 0.1 to 1.0 g/m² of treated surface.

3. The method of claim 1 wherein the amount of natamycin is about 0.25 g/m² of treated surface.

4. The method of claim 1 wherein the natamycin is applied as an aqueous suspension.

5. The method of claim 1 wherein the natamycin is applied as a micronized powder.

6. The method of claim 1 wherein natamycin is in combination with at least one member of the group consisting of a preservative and a wetting agent.

* * * * *